US00RE39794E

(19) United States
(12) Reissued Patent
Sutton et al.

(10) Patent Number: US RE39,794 E
(45) Date of Reissued Patent: Aug. 21, 2007

(54) PROCESS FOR THE SIMULTANEOUS PRODUCTION OF MALEIC ANHYDRIDE AND ITS HYDROGENATED DERIVATIVES

(75) Inventors: David Mark Sutton, Kingston-upon-Thames (GB); Andrew George Hiles, Amersham (GB); Adrian Francis Backes, London (GB)

(73) Assignee: Davy Process Technology Limited, London (GB)

(21) Appl. No.: 11/229,446

(22) PCT Filed: Oct. 4, 2000

(86) PCT No.: PCT/GB00/03805

§ 371 (c)(1), (2), (4) Date: Jul. 22, 2002

(87) PCT Pub. No.: WO01/27058

PCT Pub. Date: Apr. 19, 2001

Related U.S. Patent Documents

Reissue of:
(64) Patent No.: 6,620,949
Issued: Sep. 16, 2003
Appl. No.: 10/110,444
Filed: Jul. 22, 2002

(30) Foreign Application Priority Data

Oct. 12, 1999 (EP) ..... 99308020

(51) Int. Cl.
*C07D 307/36* (2006.01)
*C07D 307/02* (2006.01)
*C07D 307/26* (2006.01)
*C07C 29/132* (2006.01)

(52) U.S. Cl. ..... 549/262; 549/295; 549/325; 549/326; 549/429; 549/508; 568/864

(58) Field of Classification Search ..... 549/262, 549/295, 325, 326, 429, 508; 568/864
See application file for complete search history.

(56) References Cited

U.S. PATENT DOCUMENTS 2,574,644 A * 11/1951 Landau ..... 549/250
6,075,153 A * 6/2000 Bergfeld et al. ..... 549/325
6,090,245 A * 7/2000 Brown et al. ..... 203/49
6,093,835 A * 7/2000 Sawaki et al. ..... 549/259
6,127,552 A * 10/2000 Giannessi et al. ..... 549/295
6,191,322 B1 * 2/2001 Bertola ..... 568/864
6,274,743 B1 * 8/2001 Tuck et al. ..... 549/295
6,380,402 B1 * 4/2002 Cho et al. ..... 549/325
6,433,193 B1 * 8/2002 Bertola et al. ..... 549/295
6,492,535 B1 * 12/2002 Castiglioni et al. ..... 549/325
6,515,148 B1 * 2/2003 Schiødt ..... 549/326

FOREIGN PATENT DOCUMENTS

GB 2207914 * 2/1989
WO 9743234 * 11/1997
WO 9743242 * 11/1997
WO 9948852 * 9/1999

* cited by examiner

*Primary Examiner*—Deborah C. Lambkin
(74) *Attorney, Agent, or Firm*—Davidson, Davidson & Kappel, LLC

(57) ABSTRACT

A process is described for the co-production of maleic anhydride and at least one $C_4$ compound selected from butane-1,4-diol, γ-butyrolactone, and tetrahydrofuran in which maleic anhydride is produced by partial oxidation of a hydrocarbon feedstock selected from $C_4$ hydrocarbons and benzene to yield a vaporous reaction effluent stream comprising maleic anhydride, water, unconverted hydrocarbon feedstock, and carbon oxides. A part of the maleic anhydride present in the vaporous reaction effluent stream is condensed to form a crude maleic anhydride stream and leave a residual vaporous stream containing residual amounts of maleic anhydride. Further maleic anhydride is absorbed from the residual vaporous stream by absorption in an organic solvent, water or an aqueous solution. Maleic anhydride is then recovered from the loaded liquid absorptions medium. Said at least one $C_4$ compound is produced by hydrogenation of a $C_{4+}$ hydrogenation feedstock selected from maleic anhydride, maleic acid, dialkyl maleates, and mixtures of two or more thereof. The process is characterised in that material of the crude maleic anhydride stream is used as the $C_{4+}$ hydrogenation feedstock or is used to prepare the $C_{4+}$ hydrogenation feedstock.

42 Claims, 2 Drawing Sheets

Figure 1:
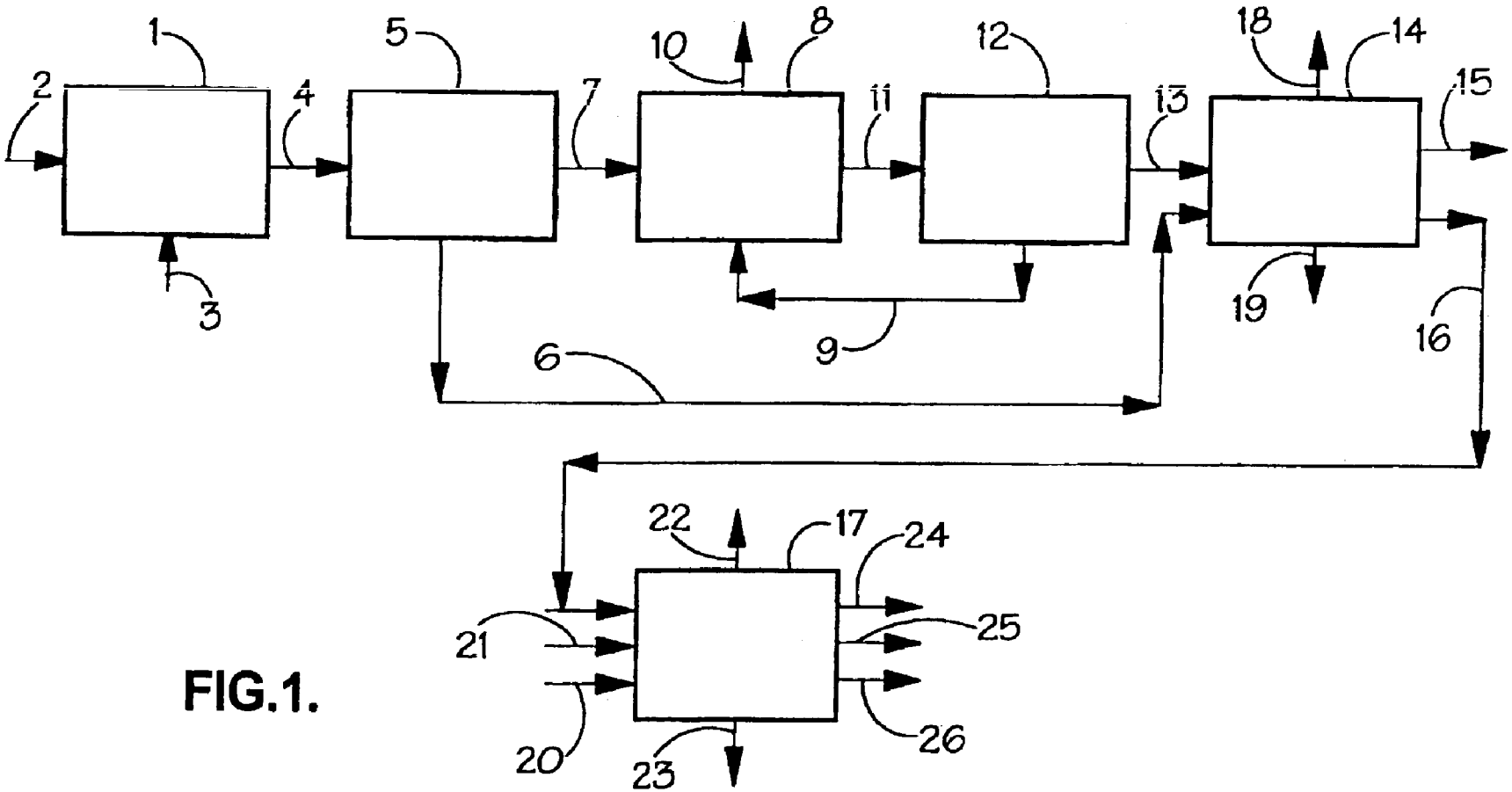

PROCESS FOR THE SIMULTANEOUS PRODUCTION OF MALEIC ANHYDRIDE AND ITS HYDROGENATED DERIVATIVES

Matter enclosed in heavy brackets [ ] appears in the original patent but forms no part of this reissue specification; matter printed in italics indicates the additions made by reissue.

This application is a 371 of PCT/GB00/03805, filed Oct. 4, 2000.

This invention relates to a process for the co-production of $C_4$ compounds, more specifically maleic anhydride, butane-1,4-diol, γ-butyrolactone, and tetrahydrofuran, from a hydrocarbon feedstock selected from $C_4$ hydrocarbons and benzene.

Maleic anhydride can be produced by vapour phase oxidation of a hydrocarbon feedstock, such as benzene, mixed $C_4$ olefins, or n-butane, in the presence of a partial oxidation catalyst.

Depending on the nature of the feedstock a supported promoted vanadium pentoxide catalyst is typically used, while the reaction temperature is usually from about 350° C. to about 500° C. and the reaction pressure is from about $10^5$ Pa to about $3\times10^5$ Pa. A substantial excess amount of air may be used in order to stay outside the explosive limits. The contact time is about 0.1 s. Alternatively it is possible, according to more modern practice, to design the plant so that satisfactory safe operation can be achieved, despite the fact that the feed mixture of air and hydrocarbon feedstock is within the flammable limits.

One design of reactor for such partial oxidation reactions comprises a tubular reactor including vertical tubes surrounded by a jacket through which a molten salt is circulated in order to control the reaction temperature. However, other designs of reactor can be used instead, including fixed bed reactors, fluidised bed reactors, or moving bed reactors.

In each case a hot vaporous reaction mixture is recovered from the exit end of the reactor which comprises maleic anhydride vapour, water vapour, carbon oxides, oxygen, nitrogen, and other inert gases, besides organic impurities such as acetic acid, acrylic acid, and unconverted hydrocarbon feedstock.

It is usual to recover and purify the maleic anhydride from this dilute reactor effluent stream in up to four steps. First, in an optional step, some conventional processes condense out part of the maleic anhydride by cooling the reactor effluent stream, typically to about 150° C. using a steam-producing heat exchanger and then cooling it further to about 60° C. by cooling it against water, in order to condense part of the maleic anhydride, typically about 30% to about 60% of the maleic anhydride present. Only partial condensation is effected because of the presence of water which reacts with maleic anhydride in the reactor effluent stream to form maleic acid, which may in turn isomerise to fumaric acid. Maleic acid has a melting point of 130° C., while fumaric acid has a melting point of 287° C., both of which are much higher than that of maleic anhydride (52.85° C.). As a result there is a tendency for deposits of solid maleic acid and fumaric acid to build up on the heat exchanger surfaces which require periodic removal, typically by use of water and/or sodium hydroxide solution which yields an aqueous solution that contains fumaric acid and maleic acid or their sodium salts and requires effluent treatment.

A second step that is conventionally used is to absorb essentially all of the remaining maleic anhydride from the effluent stream. The remaining gaseous effluent can then be vented to the atmosphere, possibly after incineration of carbon monoxide, unconverted hydrocarbon, and other organic compounds contained therein. In this absorption step an organic solvent can be used. Alternatively an aqueous solution can be used as the absorbent, in which case the maleic anhydride is mainly hydrolysed to form maleic acid.

Scrubbing with water or with an aqueous solution or slurry is described, for example, in U.S. Pat. No. 2,638,481. A disadvantage of such a procedure, however, is that some of the maleic acid is inevitably isomerised to fumaric acid. The byproduct fumaric acid represents a loss of valuable maleic anhydride and is difficult to recover from the process system since it tends to form crystalline masses which give rise to process fouling problems.

Because of this isomerisation problem a variety of other anhydrous organic solvents have been proposed for absorption of maleic anhydride from vaporous streams, for example, dibutyl phthalate (British Patent Specifications Nos. 727,828, 763,339, and 768,551), dibutyl phthalate containing up to 10 weight % phthalic anhydride (U.S. Pat. No. 4,118,403) normally liquid intramolecular carboxylic acid anhydrides, such as a branched chain $C_{12-15}$-alkenyl substituted succinic anhydride (U.S. Pat. No. 3,818,680), tricresyl phosphate (French Patent Specification No. 1,125,014), dimethyl terephthalate (Japanese Patent Publication No. 32-8408), dibutyl maleate (Japanese Patent Publication No. 35-7460), high molecular weight waxes (U.S. Pat. No. 3,040,059), diphenylpentachloride (U.S. Pat. No. 2,893,924), high boiling aromatic hydrocarbon solvents, such as dibenzylbenzene (French Patent Specification No. 2,285,386), dimethylbenzophenone (U.S. Pat. No. 3,850,758), polymethylbenzophenones, at least a portion of which contain at least 3 methyl groups, (U.S. Pat. No. 4,071,540), water-insoluble tertiary amines (U.S. Pat. No. 4,571,426), dialkyl phthalate esters having $C_4$ to $C_8$ alkyl groups and a total of 10 to 14 carbon atoms in both alkyl groups (U.S. Pat. No. 3,891,680), and esters of cycloaliphatic acids, for example dibutyl hexahydrophthalate (South African Patent Specification No. 80/1247).

A third step that is conventionally used is to recover the resulting solution of maleic anhydride or maleic acid from the absorbent. When the absorbent is an organic solvent, batch distillation or continuous distillation can be used to recover the maleic anhydride. On the other hand, when the absorbent liquid is water or an aqueous solution, the recovery step must include a dehydration step so as to re-convert the maleic acid back to maleic anhydride. One procedure that is used is to distil the maleic acid solution in the presence of xylene. This not only removes the water but also results in re-formation of maleic anhydride. In either event the elevated temperatures used tend to induce formation of fumaric acid which constitutes a further loss of potential product maleic anhydride.

U.S. Pat. No. 5,069,687 proposes recovery of maleic anhydride from a gaseous mixture by contact with an absorbent, following which water is removed from the enriched absorbent by contacting it with a water adsorbent or with a low humidity stripping gas. Maleic anhydride is then recovered from the dried enriched absorbent.

A growing use for maleic anhydride is in the production of butane-1,4-diol, and its co-products, i.e. γ-butyrolactone, and tetrahydrofuran. Direct hydrogenation of maleic anhydride or maleic acid to these $C_4$ compounds is proposed in U.S. Pat. Nos. 3,948,805, 4,001,282, 4,048,196, 4,083,809, 4,096,156, 4,550,185, 4,609,636, 4,659,686, 4,777,303, 4,985,572, 5,149,680, 5,347,021, 5,473,086, and 5,698,749, and in European Patent Publication No. 0373947A.

Esterification of maleic anhydride with an alkyl alcohol to yield a dialkyl maleate followed by hydrogenation of the resulting dialkyl maleate has also been proposed in order to produce butane-1,4-diol, and its co-products, γ-butyrolactone and tetrahydrofuran. Hydrogenation in the liquid phase is proposed in British Patent Specification No. 1,454,440. Vapour phase hydrogenation is taught in International Patent Publication No. WO 82/03854. Hydrogenation of a dialkyl maleate in two stages can be carried out as described in U.S. Pat. Nos. 4,584,419 and 4,751,334.

U.S. Pat. No. 4,032,458 proposes esterification of maleic acid with a $C_2$ to $C_{10}$ alkanol at elevated pressure and temperature followed by a two stage hydrogenation of the resulting dialkyl maleate using a slurry of a copper chromite catalyst and then by distillation.

U.S. Pat. No. 5,478,952 suggests a hydrogenation catalyst which can be used in aqueous solution to hydrogenate, for example, maleic acid, and which consists of a mixture of ruthenium and rhenium on carbon.

Processes and plant for the production of dialkyl maleates from maleic anhydride are described, for example, in U.S. Pat. No. 4,795,824 and in International Patent Publication No. WO 90/08127. This last mentioned document describes a column reactor containing a plurality of esterification trays each having a predetermined liquid hold-up and containing a charge of a solid esterification catalyst, such as an ion exchange resin containing pendant sulphonic acid groups.

The hydrogenation of dialkyl maleates to yield butane-1,4-diol is discussed further in U.S. Pat. Nos. 4,584,419, and 4,751,334, and International Patent Publication No. WO 88/00937.

In International Patent Publication No. WO 97/43242 a process is described in which maleic anhydride is absorbed in a high boiling solvent having a boiling point that is at least 30° C. higher than that of maleic anhydride at atmospheric pressure, for example dimethyl phthalate. Then the maleic anhydride in the resulting solution is esterified to form the corresponding di($C_1$ to $C_4$ alkyl) maleate, which is subsequently stripped from the solution using a hydrogen-containing gas stream to yield a vaporous mixture which is then subjected to vapour phase hydrogenation. A similar procedure in which the esterification step is omitted and the maleic anhydride is stripped from the solution in the high boiling solvent and subjected to vapour phase hydrogenation is described in International Patent Publication No. WO 97/43234. Further materials for use as absorption solvent are taught in International Patent Publications Nos. WO 99/25675 and WO 99/25678.

A further development of such processes is proposed in International Patent Publication No. WO 99/48852; in this development a second high boiling solvent, such as dibutyl phthalate, is used to scrub the off-gas from an absorption step in which maleic anhydride is absorbed from a crude vaporous maleic anhydride stream from a maleic anhydride plant in a first high boiling solvent, such as dimethyl phthalate.

In the prior art processes for production of butane-1,4-diol from maleic anhydride it is normal procedure to utilise a substantially pure maleic anhydride feedstock which contains at most a trace each of light acids (e.g. acetic acid and acrylic acid), of fumaric acid and of maleic acid.

It is an object of the present invention to provide an improved process for the co-production of maleic anhydride and the $C_4$ compounds, butane-1,4-diol, γ-butyrolactone, and tetrahydrofuran. It is also an object of the present invention to improve the yield of such $C_4$ compounds from a given quantity of hydrocarbon feedstock and hence to make these compounds more readily available and to reduce the quantity of waste products produced. It is also an object of the present invention to provide a process for the production of the $C_4$ compounds, maleic anhydride, butane-1,4-diol, γ-butyrolactone, and tetrahydrofuran from a hydrocarbon feedstock which can be operated in a plant that is more economical to construct and to run than conventional plants.

According to the present invention there is provided a process for the co-production of maleic anhydride and at least one $C_4$ compound selected from butane-1,4-diol, γ-butyrolactone, and tetrahydrofuran wherein:

maleic anhydride is produced by steps comprising:

(i) supplying a source of gaseous oxygen and a hydrocarbon feedstock selected from $C_4$ hydrocarbons and benzene to a catalytic partial oxidation zone which contains a charge of a partial oxidation catalyst capable of effecting the partial oxidation of the hydrocarbon feedstock to form maleic anhydride and which is maintained under catalytic partial oxidation conditions;

(ii) recovering from the partial oxidation zone a vaporous reaction effluent stream comprising maleic anhydride, water, unconverted hydrocarbon feedstock, and carbon oxides;

(iii) condensing a part of the maleic anhydride present in the vaporous reaction effluent stream in a condensation zone to form a crude maleic anhydride stream;

(iv) recovering from the condensation step (iii) a residual vaporous stream containing residual amounts of maleic anhydride;

(v) absorbing further maleic anhydride from the residual vaporous stream of step (iv) by absorption in a liquid absorption medium selected from an organic solvent, water, and an aqueous solution;

(vi) recovering from the absorption step (v) a loaded liquid absorption medium; and (vii) recovering maleic anhydride from the loaded liquid absorption medium; and wherein:

said at least one $C_4$ compound selected from butane-1,4-diol, γ-butyrolactone, and tetrahydrofuran is produced by steps comprising:

(viii) providing a $C_{4+}$ hydrogenation feedstock selected from maleic anhydride, maleic acid, dialkyl maleates, and mixtures of two or more thereof;

(ix) supplying said $C_{4+}$ hydrogenation feedstock and hydrogen to a hydrogenation zone which contains a charge of a hydrogenation catalyst effective for catalytic hydrogenation of the $C_{4+}$ hydrogenation feedstock to yield said at least one $C_4$ product and which is maintained under catalytic hydrogenation conditions; and (x) recovering from the hydrogenation zone a hydrogenation product stream containing said at least one $C_4$ product;

characterised in that crude maleic anhydride condensate of the crude maleic anhydride stream of step (iii) is used as the $C_{4+}$ hydrogenation feedstock of step (viii) or is used to prepare the $C_{4+}$ hydrogenation feedstock of step (viii).

The source of gaseous oxygen may comprise substantial amounts of inert gases, such as nitrogen, in addition to oxygen. Air is a convenient source of gaseous oxygen for use in the process of the invention. Hence the vaporous reaction effluent stream of step (ii) may contain nitrogen and oxygen in addition to the other components mentioned. It will often be expedient to cool the vaporous reaction effluent stream of step (ii) prior to attempting to effect condensation in step (iii).

In a preferred process according to the invention all of the crude maleic anhydride reaction product of step (iii) is used as the $C_{4+}$ hydrogenation feedstock of step (viii) or is used to prepare the $C_{4+}$ hydrogenation feedstock of step (viii).

If necessary, at least some of the maleic anhydride recovered in step (vii) can be used as or to prepare further $C_{4+}$ hydrogenation feedstock for use in step (viii).

Alternatively, if the liquid absorption medium used in step (v) is water or an aqueous solution so that the loaded absorption solution contains maleic acid, at least some of the maleic acid present in the loaded absorption medium can be used as or to prepare further $C_{4+}$ hydrogenation feedstock for use in step (viii). In this case at least some of said resulting maleic acid can first be concentrated by removal of excess water prior to use in step (viii). Moreover maleic acid present in the loaded absorption medium, whether excess water is removed for concentration purposes or not, can be mixed with crude maleic anhydride of step (iii) for use as or to prepare the $C_{4+}$ hydrogenation feedstock of step (viii).

In a preferred process according to the invention, condensation of maleic anhydride is effected in step (iii) by indirect cooling against a cooling medium selected from water and a process fluid. In an alternative preferred process condensation of maleic anhydride is effected in step (iii) in the presence of a liquid condensation medium comprising a liquid selected from maleic anhydride, monoesters of maleic acid, diesters of maleic acid, and mixtures of two or more thereof, in order to reduce the fouling of the condenser surfaces. Thus direct cooling may be carried out by spraying the liquid condensation medium into the vaporous reactant effluent stream so as to form a mixture of crude maleic anhydride and said liquid condensation medium which is used as or to prepare the $C_{4+}$ hydrogenation feedstock of step (viii). Such monoesters and diesters can be derived, for example, from $C_1$ to $C_4$ alkyl alcohols such as methanol and ethanol. Moreover the liquid condensation medium can also contain small amounts, e.g. up to about 5 molar %, of the corresponding monoalkyl and dialkyl fumarates.

In one particularly preferred process the $C_{4+}$ hydrogenation feedstock is a dialkyl maleate which is prepared by reaction of maleic anhydride with an alkyl alcohol to form a monoalkyl maleate which is then esterified with further alkyl alcohol to form a dialkyl maleate. In this case the alkyl alcohol can be methanol or ethanol and the dialkyl maleate can be dimethyl maleate or diethyl maleate. In this case the hydrogenation catalyst of step (ix) is preferably selected from copper chromite and promoted copper catalysts, such as manganese promoted copper catalysts.

In an alternative preferred process according to the invention the $C_{4+}$ hydrogenation feedstock is maleic anhydride. In this case the catalyst can be any one of those proposed for the purpose in the prior art, for example one of the catalysts disclosed in one of the aforementioned U.S. Pat. Nos. 3,948,805, 4,001,282, 4,048,196, 4,083,809, 4,096,156, 4,550,185, 4,609,636, 4,659,686, 4,777,303, 4,985,572, 5,149,680, 5,473,086, 5,478,952, and 5,698,749.

Conveniently the source of gaseous oxygen is air. However, mixtures of nitrogen and air, mixtures of off gas and air, mixtures of off gas and oxygen, pure oxygen, and oxygen-enriched air may also be mentioned as the source of oxygen. The off gas may comprise that part of the residual vaporous gas that remains after absorption of further maleic anhydride in the liquid absorption medium in step (v). The source of gaseous oxygen may be used in excess so as to maintain the mixture of hydrocarbon feedstock and source of gaseous oxygen, e.g. air, outside flammable limits. Alternatively the process may be operated so that the mixture is within flammable limits.

In one particularly preferred process the hydrocarbon feedstock is a butane feedstock.

In this case the partial oxidation catalyst may comprise a vanadium-phosphorus-oxide catalyst. Such a catalyst is sometimes described as vanadyl pyrophosphate. In order to maintain the activity of the catalyst volatile organophosphorus compounds can be bled into the feed mixture to the catalytic partial oxidation zone. As some phosphorus compounds may be present in the vaporous reaction effluent stream of step (ii) of the process of the invention which may deactivate the hydrogenation catalyst of step (ix), a guard bed of a phosphorus-absorbing material, such as vanadium-containing material; conveniently a charge of spent partial oxidation catalyst, may in this case be placed in the path of the vaporous reaction stream of step (ii), after cooling thereof, in order to remove phosphorus-containing materials therefrom.

In an alternative process the feedstock comprises benzene. In this case the catalyst can be, for example, a supported vanadium pentoxide catalyst which may be modified with molybdenum oxide.

The catalytic partial oxidation zone may be of any suitable design, for example it may be a fixed bed reactor, a tubular reactor, a fluidised bed reactor, or a moving bed reactor.

Step (v) of the process of the invention may comprise absorbing vaporous maleic anhydride from the effluent stream in an organic solvent, such as a dialkyl phthalate or a dialkyl hexahydrophthalate, for example dimethyl phthalate, dibutyl phthalate, dimethyl hexahydrophthalate, or dibutyl hexahydrophthalate. Water or an aqueous solution of maleic acid can alternatively be used to absorb vaporous maleic anhydride from the effluent stream in step (v).

In the process of the invention some of the maleic anhydride recovered in step (vii) may be used as, or may be used to make, additional $C_{4+}$ hydrogenation feedstock of step (viii).

It will often be preferred, during shutdown, to use an alkyl alcohol as wash liquor to wash condensation surfaces of the condensation zone to remove deposits of fumaric acid thereon and to combine the resulting solution with the $C_{4+}$ hydrogenation feedstock. This procedure has the advantage of avoiding or reducing the use of sodium hydroxide and the production of aqueous byproduct streams containing maleic acid or sodium maleate which are a feature of washing procedures using water and/or sodium hydroxide solution to remove fouling deposits of maleic acid and fumaric acid from condenser surfaces.

Figure 2:
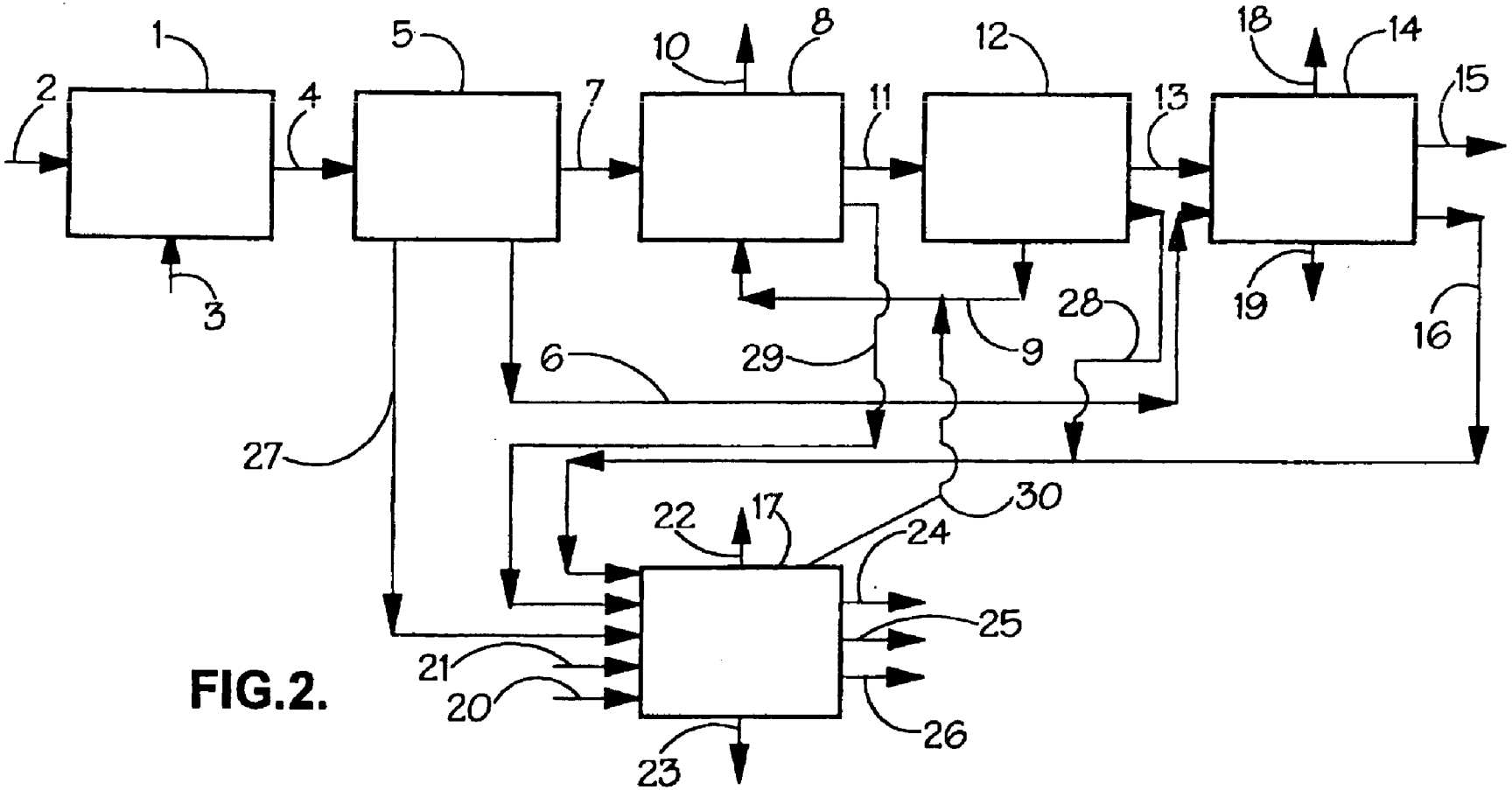

In order that the invention may be clearly understood and readily carried into effect a conventional plant for co-production of maleic anhydride and of the $C_4$ products, butane-1,4-diol, γ-butyrolactone, and tetrahydrofuran and a plant for the same purpose built according to the teachings of the invention will now be described, by way of example only, with reference to the accompanying drawings, wherein:

FIG. 1 is a flow diagram of a conventionally designed plant for the co-production of maleic anhydride and of the $C_4$ products, butane-1,4-diol, γ-butyrolactone, and tetrahydrofuran; and FIG. 2 is a similar flow diagram of a plant constructed in accordance with the teachings of the invention and intended for the same purpose.

It will be appreciated by those skilled in the art that, since the accompanying drawings are diagrammatic, many other items of equipment which are not shown in the drawings would be required in an actual plant. Such additional items of equipment are conventional in nature and include (but are not limited to) distillation columns, reactors, condensers, pumps, holding tanks, valves, pressure sensors, temperature sensors, pressure controllers, temperature controllers, level sensors, heaters, coolers, surge tanks, condensers, column reboilers, and the like. Any such additional items of equipment would be installed in accordance with conventional engineering practice and form no part of the present invention.

Referring to FIG. 1 of the drawings, a partial oxidation unit 1 comprises a partial oxidation reactor containing a charge of a partial oxidation catalyst, for example a vanadium-containing catalyst such as vanadium-phosphorus-oxide (whose catalytically active phase has been reported to be vanadyl pyrophosphate, $(VO)_2P_2O_7$). Unit 1 can be of fixed bed or fluidised bed design and is supplied with a superheated $C_4$ hydrocarbon feedstock, such as butane, by means of line 2 and with air by means of line 3. The butane:air volume ratio is typically from about 20:1. The catalyst charge in partial oxidation unit 1 is maintained under a pressure of from about 100 kPa to about 200 kPa.

In partial oxidation unit 1 butane is converted by partial oxidation to maleic anhydride. The main byproducts are carbon monoxide, carbon dioxide, and water:

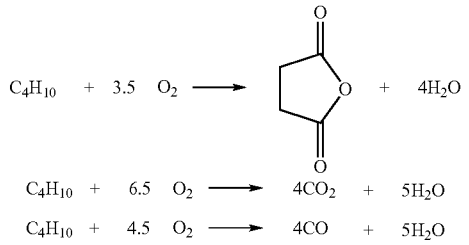

All three reactions are highly exothermic.

For further details of suitable designs of partial oxidation unit for production of maleic anhydride reference may be made to Kirk-Othmer Encyclopedia of Chemical Technology, Fourth Edition, Volume 15, pages 893 to 928.

A hot vaporous partial oxidation reaction product stream is recovered from partial oxidation unit in line 4. This is at a temperature of from about 390° C. to about 430° C. and contains nitrogen, oxygen, unreacted butane, water, carbon oxides, maleic anhydride, maleic acid, fumaric acid, and traces of acetic acid, and acrylic acid. The reaction product stream is then cooled before it is fed to a condensation stage 5 which is maintained at a temperature below the dew point of the partial oxidation product stream so as to cause from about 20% to about 60%, preferably from about 40% to about 60%, of the maleic anhydride present in line 4 to condense. Typically condensation stage 5 includes two coolers, the first operating at about 150° C. and the second at about 60° C. The resulting condensate is recovered in line 6.

The residual maleic anhydride, which is still in vaporous form, passes on in line 7 to an absorption unit 8, for example a gas scrubber unit, through which the vapour stream is passed upward in countercurrent to a down flowing stream of an organic solvent, such as dibutyl phthalate, supplied from line 9. The residual gas exits absorption unit 8 in line 10 and can be vented, typically via an off gas incinerator, while the resulting solution of maleic anhydride is recovered in line 11 and passed to a solvent recovery unit 12. In recovery unit 12 the solvent is separated from the maleic anhydride, conveniently by distillation under normal or reduced pressure. The recovered solvent is recycled in line 9 while the separated maleic anhydride is passed on by way of line 13 to a purification unit 14 for further purification, for example by batch distillation. Some of the resulting product maleic anhydride is recovered in line 15 while the remainder is passed by means of line 16 to a butane-1,4-diol plant 17.

Reference numerals 18 and 19 represent lines for the recovery of light impurities and heavy impurities respectively.

In the butane-1,4-diol plant 17 maleic anhydride is reacted with an alkyl alcohol, such as methanol, to form a monoalkyl maleate, such as monomethyl maleate, which is then reacted further in a countercurrent reactor column of the type described in European Patent Publication No. 0454719A for substantially complete conversion to dimethyl maleate.

The reactions concerned are:

(1)

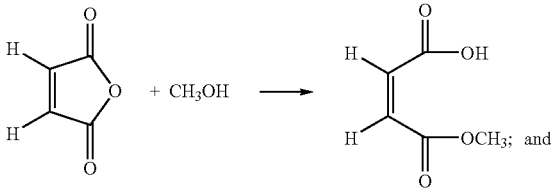

(2)

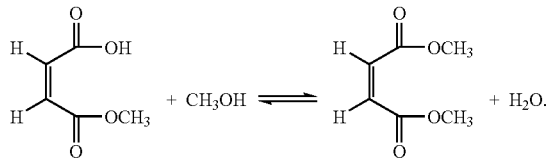

The monoesterification reaction (1) is autocatalytic but reaction (2) is preferably conducted in the presence of an acidic esterification catalyst such as an ion exchange resin containing sulphonic acid groups. For further details the attention of the reader is directed to European Patent Publication No. 0454719A. Other specifications describing production of dialkyl maleates are European Patent Specification Nos. 0255399A and 0255401A. The resulting dimethyl maleate is then hydrogenated in the vapour phase using a copper chromite catalyst or a promoted copper catalyst, such as a manganese promoted catalyst of the type disclosed in European Patent Publication No. 0656336A, to yield butane-1,4-diol and, as co-products, γ-butyrolactone and tetrahydrofuran.

In addition the hydrogenation product mixture will normally contain minor amounts of the corresponding dialkyl succinate, n-butanol, water, and a cyclic acetal, i.e. 2-(4'-hydroxybutoxy)-tetrahydrofuran of the formula:

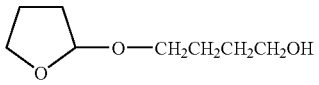

The mechanisms for formation of all these products and by-products have not been fully elucidated. However, their production is consistent with the following reaction scheme:

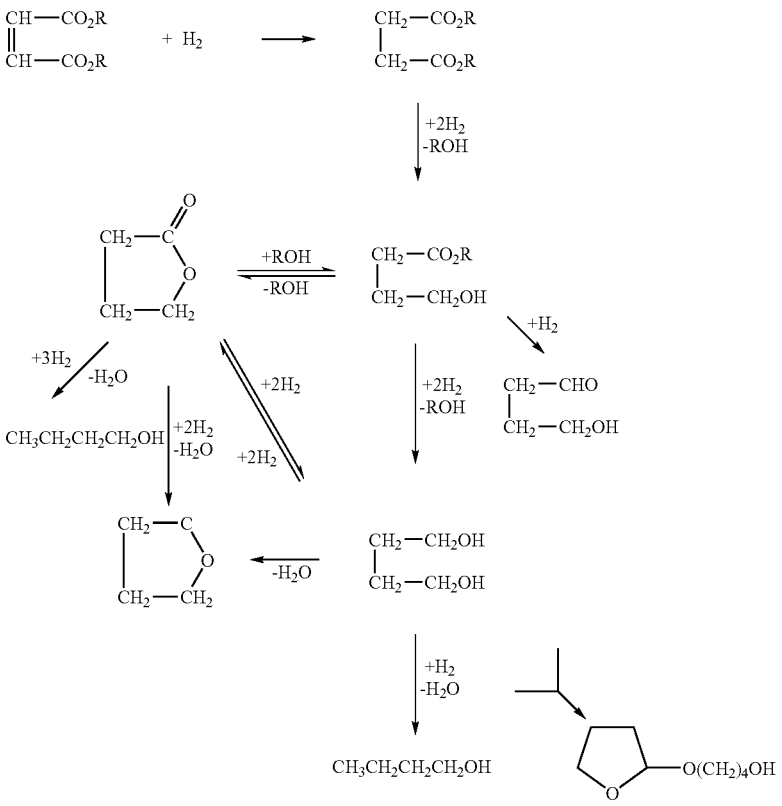

wherein R is methyl. The methanol released in the course of the hydrogenation step is condensed and separated from the other condensable components, including butane-1,4-diol, γ-butyrolactone, tetrahydrofuran, water and by-products including n-butanol. For further information regarding methods of separating the condensable components of the hydrogenation reactions, reference may be made, for example, to International Patent Publications Nos. WO 91/01981 and WO 97/36846. The recovered methanol can be recycled for production of further dimethyl maleate. Typical hydrogenation conditions include use of an $H_2$:dimethyl maleate molar ratio of from about 100:1 to about 400:1, for example about 320:1, a temperature of from about 150° C. to about 240° C., and a pressure of from about 5 bar ($5\times10^5$ Pa) to about 100 bar ($10^7$ Pa), depending upon the desired butane-1,4-diol: γ-butyrolactone product ratio.

Reference numeral 20 indicates a supply line for supplying methanol to the butane-1,4-diol plant 17, while line 21 is the hydrogen supply line for supply of the hydrogen needed for hydrogenation of dimethyl maleate. A purge gas stream is taken in line 22 while water and other by-products, including n-butanol and heavy byproducts are recovered by way of line 23. Reference numerals 24, 25, and 26 indicate lines for the recovery of butane-1,4-diol, γ-butyrolactone, and tetrahydrofuran, respectively.

FIG. 2 illustrates a plant constructed in accordance with the teachings of the invention. In FIG. 2 like reference numerals are used to indicate like parts to those present in the plant of FIG. 1.

In the plant of FIG. 2 the process for the production of maleic anhydride is essentially the same as that of FIG. 1. However, instead of supplying substantially pure maleic anhydride in line 16 to the butane-1,4-diol plant 17, this is instead supplied with crude maleic anhydride condensate from condensation unit 5 by way of line 27. In addition it can also be supplied, as and when necessary, with partially refined or pure maleic anhydride in line 28 from solvent recovery unit 12. Hence when the demand for butane-1,4-diol, γ-butyrolactone and/or tetrahydrofuran rises beyond the output determined by the flow rate of maleic anhydride in line 27, some of the maleic anhydride from solvent recovery unit 12 can be diverted to the butane-1,4-diol plant 17 to make up the shortfall.

Instead of using an organic solvent, such as dibutyl phthalate, in absorption unit 8 an aqueous absorbent, such as water or an aqueous solution of maleic acid, can alternatively be used. In this case the stream in line 11 will be an aqueous solution of maleic acid, while recovery unit 12 is a dehydration unit in which the aqueous solution of maleic acid is subjected to dehydration either by heating or by distillation in the presence of xylene to regenerate maleic anhydride, the water released by dehydration of maleic acid as well as the water of the absorbent being recovered as an overhead product and recycled back in line 9 to absorption unit 8.

It is alternatively possible to effect condensation of part of the maleic anhydride present in the hot partial oxidation product stream from partial oxidation unit 4 in the presence of a cooled stream of maleic anhydride or other $C_{4+}$ hydrogenatable material, such as a monoalkyl maleate (e.g. monomethyl maleate), dialkyl maleate (e.g. dimethyl maleate), or a mixture of two or more thereof. At least a part of this stream can then be passed to the butane-1,4-diol plant 17. The remainder can be cooled and used again for condensation. Alternatively the entire stream can be passed forward to the butane-1,4-diol unit 17 for conversion of the maleic anhydride present therein to dimethyl maleate, some of which is then recycled for condensation of further maleic anhydride. An advantage of such a procedure is that fouling of surfaces in the condensation stage may be reduced.

It is further possible to feed some of the solution from absorption unit 8, by way of line 29 to the butane-1,4-diol plant. Any impurities present in the crude maleic acid or maleic anhydride of the streams in line 27 or line 29 are separated out in the course of the processing steps used in butane-1,4-diol plant 17. Recovered solvent is returned in line 30 to line 9.

The condensed crude maleic anhydride stream present in line 27 of the plant of FIG. 2 contains [as] impurities which are not normally present in the purified maleic anhydride feedstock in line 16 of the plant of FIG. 1. Such impurities comprise light boiling impurities (such as acetic acid and acrylic acid), heavy impurities, and maleic anhydride derivatives (including maleic acid and fumaric acid). When the crude maleic anhydride is esterified prior to hydrogenation, the acidic light boiling impurities will also be esterified, as well as the maleic anhydride derivatives. The resulting light boiling esters, such as methyl acetate or ethyl acetate and methyl acrylate or ethyl acrylate, can be stripped from the resulting dialkyl maleate (e.g. dimethyl maleate or diethyl maleate) overhead, along with the water of esterification when using, for example, the procedure described in European Patent Publication No. 0454719A. Esterification of the maleic anhydride derivatives will produce a corresponding additional amount of the corresponding dialkyl maleate. Heavy boiling impurities will pass through the esterification reactor along with the dialkyl maleate and will be fed to the hydrogenation vaporiser, when vapour phase hydrogenation is used. The hydrogenation vaporiser can be operated so as to vaporise the dialkyl maleate only partially and to recycle the unvaporised material back to the vaporiser, thereby concentrating the heavy impurities in the unvaporised material and enabling the heavy impurities to be removed in a purge stream.

In the case when the $C_{4+}$ hydrogenation feedstock is the crude maleic anhydride stream, then the light impurities are also hydrogenated in the hydrogenation step and result in light hydrogenation products including ethanol and propanol, which can be removed from the hydrogenation product as an overhead product by distillation. Heavy impurities and heavy impurity hydrogenation products can be separated by conventional distillation techniques as a bottom product from the crude hydrogenation product. Maleic anhydride derivatives, such as maleic acid and fumaric acid, are hydrogenated to form a corresponding additional amount of butane-1,4-diol, γ-butyrolactone, and tetrahydrofuran.

The novel process of the invention has the important benefit that the capital cost of the plant can be significantly reduced because it is necessary to recover only about a half (typically about 40% to about 60%) of the maleic anhydride in line 4. Hence the subsequent solvent recovery unit 12 and the purification section 14 can be correspondingly reduced in size and can be operated with reduced operating costs.

The process of the invention also results in a higher efficiency of maleic anhydride usage because less maleic anhydride is lost as fumaric acid. Instead such fumaric acid is largely contained in the crude condensate in line 27 and is converted to butane-1,4-diol, γ-butyrolactone and/or tetrahydrofuran in butane-1,4-diol plant 17.

Vanadium-phosphorus-oxide based catalysts are unstable in that they tend to lose phosphorus over time at reaction temperatures, this loss of phosphorus having a tendency to accelerate if hot spots should develop in a fixed bed reactor. Accordingly it may often be expedient to add a volatile organophosphorus compound to the partial oxidation catalyst with a view to providing catalyst activity stabilisation. In the course of time volatile phosphorus compounds escape from the catalyst and appear in the vaporous reaction effluent stream from the partial oxidation unit. Since phosphorus is a potential catalyst poison or inhibitor for the hydrogenation catalyst used in the butane-1,4-diol unit 17 of the plant of FIG. 2, it is preferable in this case to include a guard bed of a phosphorus-absorbing material in line 4 to absorb any traces of phosphorus-containing material that would otherwise have a deleterious effect upon the hydrogenation catalyst of butane-1,4-diol unit 17. Conveniently such a guard bed can be a bed of spent vanadium-containing partial oxidation catalyst. The temperature in such a guard bed should be as low as possible in order to maximise phosphorus absorption but above the condensation point for maleic anhydride in the stream of line 4.

The condensation surfaces of condensation unit 5 may become fouled with deposits of maleic acid and fumaric acid. It is preferred to wash these with methanol. The resulting methanolic solution containing fumaric acid, maleic acid, and maleic anhydride, besides monomethyl maleate and dimethyl maleate formed by esterification, can be supplied as part of the feed to butane-1,4-diol unit 17. This has the advantage, compared with the potentially hazardous conventional water washing procedure using water and/or sodium hydroxide solution that production of an aqueous solution of maleic acid and fumaric acid or sodium maleate and sodium fumarate is avoided.

In an alternative form of the process of the invention the $C_{4+}$ hydrogenation feedstock is maleic anhydride or maleic acid instead of a dialkyl maleate, such as dimethyl maleate. In this case butane-1,4-diol plant 17 comprises a hydrogenation unit containing a hydrogenation catalyst, for example one of the catalysts disclosed in the prior art as represented, for example, by the aforementioned U.S. Pat. Nos. 3,948,805, 4,001,282, 4,048,196, 4,083,809, 4,096,156, 4,550,185, 4,609,636, 4,659,686, 4,777,303, 4,985,572, 5,149,680, 5,473,086, 5,478,952, and 5,698,749. Such catalysts are preferably used under the appropriate reaction conditions as disclosed in those prior art specifications. The disclosures of all specifications mentioned above are herein incorporated by reference.

What is claimed is:

1. A process for the co-production of maleic anhydride and at least one $C_4$ compound selected from the group consisting of butane-1,4-diol, γ-butyrolactone and tetrahydrofuran wherein:

maleic anhydride is produced by steps comprising:

supplying a source of gaseous oxygen and a hydrocarbon feedstock selected from $C_4$ hydrocarbons and benzene to a catalytic partial oxidation zone which contains a charge of a partial oxidation catalyst capable of effecting the partial oxidation of the hydrocarbon feedstock to form maleic anhydride and which is maintained under catalytic partial oxidation conditions;

(ii) recovering from the partial oxidation zone a vaporous reaction effluent stream comprising maleic anhydride, water, unconverted hydrocarbon feedstock, and carbon oxides;

(iii) condensing a part of the maleic anhydride present in the vaporous reaction effluent stream in a condensation zone to form a crude maleic anhydride stream;

(iv) recovering from the condensation step (iii) a residual vaporous stream containing residual amounts of maleic anhydride;

(v) absorbing further maleic anhydride from the residual vaporous stream of step (iv) by absorption in a liquid absorption medium selected from an organic solvent, water, and an aqueous solution;

(vi) recovering from the absorption step (v) a loaded liquid absorption medium; and (vii) recovering maleic anhydride from the loaded liquid absorption medium;

and wherein[:]

said at least one $C_4$ compound selected from the group consisting of butane-1,4-diol, γ-butyrolactone and tetrahydrofuran is produced by steps comprising:

(viii) providing a $C_{4+}$ hydrogenation feedstock selected from maleic anhydride, maleic acid, dialkyl maleates, *monoalkyl maleates* and mixtures of two or more thereof;

(ix) supplying said $C_{4+}$ hydrogenation feedstock and hydrogen to a hydrogenation zone which contains a charge of a hydrogenation catalyst effective for catalytic hydrogenation of the $C_{4+}$ hydrogenation feedstock to yield said at least one $C_4$ product and which is maintained under catalytic hydrogenation conditions; and (x) recovering from the hydrogenation zone a hydrogenation product stream containing said at least one $C_4$ product;

wherein [crude maleic anhydride condensate of the crude maleic anhydride stream of] *condensation of maleic anhydride is effected in* step (iii) *in the presence of a liquid condensation medium consisting of a liquid selected from the group consisting of maleic anhydride, monoesters of maleic acid, diesters of maleic acid, and mixtures of two or more thereof, wherein the crude maleic anhydride stream of step (iii)* is used as the $C_{4+}$ hydrogenation feedstock of step (viii) or is used to prepare the $C_{4+}$ hydrogenation feedstock of step (viii).

2. A process according to claim 1, wherein all of the crude maleic anhydride stream of step (iii) is used as the $C_{4+}$ hydrogenation feedstock of step (viii) or is used to prepare the $C_{4+}$ hydrogenation feedstock of step (viii).

3. A process according to claim 1, wherein at least some of the maleic anhydride recovered in step (vii) is used [as or] to prepare further $C_{4+}$ hydrogenation feedstock for use in step (viii).

4. A process according to claim 1, wherein the liquid absorption medium used in step (v) is selected from water and an aqueous solution so that the loaded absorption solution contains maleic acid and that at least some of the maleic acid present in the loaded absorption medium is used [as or] to prepare further $C_{4+}$ hydrogenation feedstock for use in step (viii).

5. A process according to claim 4, wherein at least some of said resulting maleic acid is first concentrated by removal of excess water prior to use in step (viii).

6. A process according to claim 4, wherein maleic acid present in the loaded absorption medium is mixed with crude maleic anhydride of step (iii) for use as or to prepare the $C_{4+}$ hydrogenation feedstock of step (viii).

7. A process according to claim 1, wherein step (v) comprises absorbing vaporous maleic anhydride from the effluent stream in an organic solvent.

8. A process according to claim 7, wherein the organic solvent is a dialkyl phthalate or a dialkyl hexahydrophthalate.

[9. A process according to claim 1, wherein in step (iii) condensation of maleic anhydride is effected by indirect cooling against a cooling medium selected from water and a process fluid.]

10. A process according to claim 1, wherein in step (iii) [condensation of maleic anhydride] *said liquid condensation medium* is [effected in the presence of a liquid condensation medium selected from maleic anhydride, monoesters of maleic acid, and diesters of maleic acid, said liquid condensation medium being] sprayed into the vaporous reactant effluent stream so as to form a mixture of crude maleic anhydride and said liquid condensation medium which is used as, or to prepare, the $C_{4+}$ hydrogenation feedstock of step (viii).

11. A process according to claim 1, wherein the $C_{4+}$ hydrogenation feedstock is a dialkyl maleate which is prepared by reaction of maleic anhydride with an alkyl alcohol to form a monoalkyl maleate which is then esterified with further alkyl alcohol to form a dialkyl maleate.

12. A process according to claim 11, wherein the alkyl alcohol is methanol and the dialkyl maleate is dimethyl maleate.

13. A process according to claim 11, wherein the hydrogenation catalyst of step (ix) is selected from copper chromite and promoted copper catalysts.

14. A process according to claim 1, wherein the $C_{4+}$ hydrogenation feedstock is maleic anhydride.

15. A process according to claim 1, wherein the source of gaseous oxygen is air or a mixture of oxygen and recycle off gas.

16. A process according to claim 1, wherein the hydrocarbon feedstock is a butane feedstock.

17. A process according to claim 16, wherein the partial oxidation catalyst comprises vanadium-phosphorus oxide.

18. A process according to claim 17, wherein the vaporous reaction effluent stream is cooled prior to step (iii) and that a guard bed of a phosphorus-absorbing material is placed in the path of the cooled vaporous reaction effluent stream prior to step (iii) thereby to remove phosphorus-containing materials therefrom.

19. A process according to claim 18, wherein the phosphorus-absorbing material comprises a charge of spent vanadium-containing partial oxidation catalyst.

20. A process according to claim 1, wherein the catalytic partial oxidation zone comprises a fixed bed reactor, a tubular reactor, a fluidised bed reactor, or a moving bed reactor.

21. A process according to claim 1, wherein an alkyl alcohol is used as wash liquor to wash condensation surfaces of the condensation zone to remove deposits of maleic acid and fumaric acid thereon and that the resulting solution is combined with the $C_{4+}$ hydrogenation feedstock.

*22. A process according to claim 7, wherein the organic solvent is selected from the group consisting of dimethyl phthalate, dibutyl phthalate, dimethyl hexahydrophthalate, and dibutyl hexahydrophthalate.*

*23. A process for the co-production of maleic anhydride and at least one $C_{4+}$ compound selected from the group consisting of butane-1,4-diol, γ-butyrolactone and tetrahydrofuran wherein:*

*maleic anhydride is produced by steps comprising:*

*(i) supplying a source of gaseous oxygen and a $C_4$ hydrocarbon feedstock to a catalytic partial oxidation zone which contains a charge of a phosphorous-containing partial oxidation catalyst capable of effecting the partial oxidation of the $C_4$ hydrocarbon feedstock to form maleic anhydride and which is maintained under catalytic partial oxidation conditions;*

*(ii) recovering from the partial oxidation zone a vaporous reaction effluent stream comprising maleic anhydride, water, unconverted hydrocarbon feedstock, and carbon oxides;*

(iii) *condensing a part of the maleic anhydride present in the vaporous reaction effluent stream in a condensation zone to form a crude maleic anhydride stream;*

(iv) *recovering from the condensation step (iii) a residual vaporous stream containing residual amounts of maleic anhydride;*

(v) *absorbing further maleic anhydride from the residual vaporous stream of step (iv) by absorption in a liquid absorption medium selected from an organic solvent, water, and an aqueous solution;*

(vi) *recovering from the absorption step (v) a loaded liquid absorption medium; and*

(vii) *recovering maleic anhydride from the loaded liquid absorption medium;*

*and wherein:*

*said at least one $C_4$ compound selected from the group consisting of butane-1,4-diol, γ-butyrolactone and tetrahydrofuran is produced by steps comprising:*

(viii) *providing a $C_{4+}$ hydrogenation feedstock selected from maleic anhydride, maleic acid, monoalkyl maleates, dialkyl maleates, and mixtures of two or more thereof;*

(ix) *supplying said $C_{4+}$ hydrogenation feedstock and hydrogen to a hydrogenation zone which contains a charge of a hydrogenation catalyst effective for catalytic hydrogenation of the $C_{4+}$ hydrogenation feedstock to yield said at least one $C_{4+}$ product and which is maintained under catalytic hydrogenation conditions; and*

(x) *recovering from the hydrogenation zone a hydrogenation product stream containing said at least one $C_{4+}$ product; wherein*

*the vaporous reaction of effluent stream is cooled prior to step (iii), that a guard bed of a phosphorous-absorbing material is placed in the path of the cooled vaporous reaction effluent stream prior to step (iii) thereby to remove phosphorous-containing materials therefrom, and that material of the crude maleic anhydride stream of step (iii) is used as the $C_{4+}$ hydrogenation feedstock of step (viii) or is used to prepare the $C_{4+}$ hydrogenation feedstock of step (viii).*

*24. A process according to claim 23, wherein all of the crude maleic anhydride stream of step (iii) is used as the $C_{4+}$ hydrogenation feedstock of step (viii) or is used to prepare the $C_{4+}$ hydrogenation feedstock of step (viii).*

*25. A process according to claim 23, wherein at least some of the maleic anhydride recovered in step (vii) is used as or to prepare further $C_{4+}$ hydrogenation feedstock for use in step (viii).*

*26. A process according to claim 23, wherein the liquid absorption medium used in step (v) is selected from water and an aqueous solution so that the loaded absorption solution contains maleic acid and that at least some of the maleic acid present in the loaded absorption medium is used as or to prepare further $C_{4+}$ hydrogenation feedstock for use in step (viii).*

*27. A process according to claim 26, wherein at least some of said resulting maleic acid is first concentrated by removal of excess water prior to use in step (viii).*

*28. A process according to claim 26, wherein maleic acid present in the loaded absorption medium is mixed with crude maleic anhydride of step (iii) for use as or to prepare the $C_{4+}$ hydrogenation feedstock of step (viii).*

*29. A process according to claim 23, wherein step (v) comprises absorbing vaporous maleic anhydride from the effluent stream in an organic solvent.*

*30. A process according to claim 29, wherein the organic solvent is a dialkyl phthalate or a dialkyl hexahydrophthalate.*

*31. A process according to claim 29, wherein the solvent is selected from the group consisting of dimethyl phthalate, dibutyl phthalate, dimethyl hexahydrophthalate, and dibutyl hexahydrophthalate.*

*32. A process according to claim 23, wherein in step (iii) condensation of maleic anhydride is effected by indirect cooling against a cooling medium selected from the group consisting of water and a process fluid.*

*33. A process according to claim 23, wherein in step (iii) condensation of maleic anhydride effected in the presence of a liquid condensation medium selected from the group consisting of maleic anhydride, monoesters of maleic acid, and diesters of maleic acid, said liquid condensation medium being sprayed into the vaporous reactant effluent stream so as to form a mixture of crude maleic anhydride and said liquid condensation medium which is used as or to prepare the $C_{4+}$ hydrogenation feedstock of step (viii).*

*34. A process according to claim 23, wherein $C_{4+}$ hydrogenation feedstock is a dialkyl maleate which is prepared by reaction of maleic anhydride with an alkyl alcohol to form a monoalkyl maleate which is then esterified with further alkyl alcohol to form a dialkyl maleate.*

*35. A process according to claim 34, wherein said alkyl alcohol is methanol and said dialkyl maleate is dimethyl maleate.*

*36. A process according to claim 34, wherein the hydrogenation catalyst of step (ix) is selected from the group consisting of copper chromite and promoted copper catalysts.*

*37. A process according to claim 23, wherein the $C_{4+}$ hydrogenation feedstock is maleic anhydride.*

*38. A process according to claim 23, wherein the source of gaseous oxygen is air or a mixture of oxygen and recycle off gas.*

*39. A process according to claim 23, wherein the hydrocarbon feedstock is a butane feedstock.*

*40. A process according to claim 38, wherein the partial oxidation catalyst comprises vanadium-phosphorous oxide.*

*41. A process according to claim 23, wherein the phosphorus-absorbing material comprises a charge of spent vanadium-containing partial oxidation catalyst.*

*42. A process according to claim 23, wherein the catalytic partial oxidation zone comprises a fixed bed reactor, a tubular reactor, a fluidised bed reactor, or a moving bed reactor.*

*43. A process according to claim 23, wherein an alkyl alcohol is used as wash liquor to wash condensation surfaces of the condensation zone to remove deposits of maleic acid and fumaric acid thereon and that the resulting solution is combined with the $C_{4+}$ hydrogenation feedstock.*

* * * * *